United States Patent [19]

Heikkenen

[11] 4,373,393
[45] Feb. 15, 1983

[54] METHOD FOR DETERMINING THE AGE OR AUTHENTICITY OF TIMBER STRUCTURES

[76] Inventor: Herman J. Heikkenen, 802 Preston Ave., Blacksburg, Va. 24061

[21] Appl. No.: 926,223

[22] Filed: Jul. 19, 1978

[51] Int. Cl.³ ............................................ G01N 33/46
[52] U.S. Cl. ................................................. 73/432 R
[58] Field of Search ..................................... 73/432 R

[56] References Cited

PUBLICATIONS

U.S. Dept. of Commerce Report (1977), Tree Rings; A. Record of Climate Past–Fritts.
Science Oct. 28, 1977 pp. 399–401.
Michael et al. (ed.) Dating Techniques for the Archaebgrt The MIT Press Cambridge, Mass 1971, pp. 49–56.

Primary Examiner—S. Clement Swisher
Attorney, Agent, or Firm—John I. Iverson

[57] ABSTRACT

A method of dendrochronology. A method for determining the age or authenticity of timber structures based on a correlation of the relative growth patterns of the woods used in the timber structure and the wood in samples taken from mature living trees on one or more sites in the general vicinity of the timber structure. The method is also useful for dendrochronological studies of specific tree species and long range weather and climatic studies of a region.

1 Claim, No Drawings

METHOD FOR DETERMINING THE AGE OR AUTHENTICITY OF TIMBER STRUCTURES

BACKGROUND OF THE INVENTION

This invention relates to a dendrochronological method for the study of annual growing seasons and tree species over an extended period of time. It relates particularly to a method for accurately determining the age or authenticity of timber structures or other wooden objects. The invention is especially useful for archeological studies by which the exact age of old timber structures, such as houses, churches, bridges and the like can be easily and accurately determined.

The usual ways of dating timber structures, such as an old house, have been to use old deeds and other written documents, if available, or through the use of architectural styles and construction details. These prior techniques are frequently imperfect and inaccurate especially in very old structures where written documentation does not exist and the structure has gone through several renovations.

While there have been other dendrochronological methods and techniques tried in the past either to study the climate of a region or to attempt to date the age of old timber structures, none of these earlier methods or techniques produced results that could be considered accurate and reliable.

SUMMARY OF THE INVENTION

It is therefore an object of this invention to provide a reliable and accurate method for easily determining the age of timber structures.

It is a further object of this invention to provide a method for the dendrochronological study of various tree species.

It is a still further object of this invention to provide a method for the study of the nature of annual growing seasons in a region over an extended period of time.

Other and further objects of this invention will become apparent from the following description and claims.

It has been discovered that the foregoing objects can be attained by the method of this invention which first determines the relative tree growth pattern for trees at one or more sites in the region and then correlates the relative tree growth patterns between the sites to determine a climatic history, or with the relative tree growth pattern of the trees used for a timber structure, to determine the age of the timber structure.

DESCRIPTION OF THE PREFERRED EMBODIMENT

The preferred embodiment of this invention is a method of determining the age or authenticity of a timber structure.

The method comprises first taking a plurality of radial core samples across the grain of several portions of the timber structure using a hollow boring tool that retrieves the core samples as a thin elongated cylinder of wood. It is desirable that the core samples be obtained from several separate timbers in the structure, such as from the beams, joists or rafters, in the case of a building.

Next, similar core samples are similarly obtained from a plurality of mature living trees or trees whose death date is known, at one or more sites in the general vicinity of the timber structure. The site may be many miles away from the timber structure. Preferably, the site should be well drained and the trees selected for sampling be long life trees, such as oaks. Only one core sample from each of a representative sampling of trees at a site is necessary.

The core samples from the timber structure and the trees are then placed in a dendrochronometer or similar device and the absolute radial width of each annular growth ring is measured for each core sample. The annual growth ring widths for each sample are then tabulated by comparing the absolute width of the annular growth ring to the absolute width of the annual growth ring for the preceding year. For example, the absolute width of the 1975 ring relative to the absolute width of the 1974 ring of the core sample will be either greater (+), less (−), or equal (0). The absolute width of the 1974 ring is in turn compared to the absolute width of the 1973 ring, and so on until all the rings along the radial core sample have been measured, compared and tabulated as relative ring widths by a plus, minus or zero symbol, or other means of identification.

The relative ring widths of all the samples from a given site are then compared chronologically on a scale to determine in what years the samples show a coincidence in the nature of the relative growth among the samples taken from the same site. For the purposes of the method of this invention I have determined and define as an "index year" any year in which the width of the annular growth ring relative to the preceding ring (+, −, 0) coincides in at least 80% of the trees sampled at a given site. The chance occurrence of an index year is $(1/2)^n$, and thus with a sample size of ten $(1/2)^{10}$, the odds of an index year being a chance occurrence are at least $3.9 \times 10^{-3}$. Less than 80% coincidence greatly increases the possibility of a chance occurrence of an index year.

This type of comparison is similarly applied to the samples obtained from the timber structure and the "index years" for the structure are likewise determined on a chronological scale in a similar manner to that described above for the site samples.

The index years for site and for the structure are each expressed chronologically, either graphically or in some other manner, over the period of time covered by the samples to create an index year frequency pattern for the site and for the structure.

The site index year frequency pattern is then cross correlated with the structure index year frequency pattern to provide a best fit of coincidence between the index years of the two patterns using either well known graphical or statistical methods. This step in the method of my invention establishes a common period in the life of the trees sampled at the site and the trees that were used to make the timbers in the structure.

One needs then only to count backwards on the cross correlated chronological scale from the last growth ring of the mature living trees or the trees whose death date is known until one matches the outermost growth ring on the chronological scale of the structure timber to determine the year that the timber was cut and thus the construction date of the structure.

This method of my invention has been tested using several sites in the State of Virginia to date timbers in several old Virginia structures to within one year of their construction as verified by old deeds and other written documents.

Preferably a region will have a number of sites which have been sampled and given a chronology and an index year frequency pattern which can then be used at any time for the dating of old timber structures in that region using my method. In addition the index year frequency patterns from several sites in the region can be compared to establish a climatic history of the region for a long period of time which history will have many applications in fields of agriculture, forest management and other natural resource management, such as water resources.

I claim:

1. A method for determining the age or authenticity of a timber structure comprising:
   (a) taking a plurality of radial core samples from several portions of a timber structure,
   (b) taking at least one radial core sample from each of several mature living trees of one or more species or trees of one or more species whose death date is known, from at least one well drained, site in the general vicinity of the timber structure,
   (c) measuring the absolute radial width of each annual growth ring for each of the samples taken in steps (a) and (b),
   (d) comparing the width of each annual growth ring to the width of previous annular growth ring to determine if it is greater, less or equal in width to the previous annular growth ring, for each of the samples taken in steps (a) and (b),
   (e) comparing the samples taken in step (a) to determine index years in which the annual growth ring relative to the preceding ring coincides in at least 80 percent of the samples,
   (f) comparing the samples taken in step (b) to determine index years in which the annual growth ring relative to the preceding ring coincides in at least 80 percent of the samples,
   (g) correlating on a first chronological scale the frequency pattern of the index years determined in step (e) with the frequency pattern of the index years determined in step (f) on a second chronological scale to establish a common period in the life of trees sampled in step (b) and trees used to make the timbers sampled in step (a),
   (h) determining the last year of growth of the samples obtained in step (a) by comparing chronologically on the first chronological scale the date of the outermost growth ring of the samples taken in step (a) to the date of the outermost growth ring of the samples taken in step (b), on the second chronological scale.

* * * * *